United States Patent [19]

Nozaki et al.

[11] Patent Number: 4,997,767

[45] Date of Patent: Mar. 5, 1991

[54] YEAST SHUTTLE VECTOR

[75] Inventors: Chikateru Nozaki; Fukusaburo Hamada; Nobuya Ohtomo, all of Kumamoto, Japan

[73] Assignee: Juridical Foundation The Chemo-Sero-Therapeutic Research Institute, Kumamoto, Japan

[21] Appl. No.: 946,329

[22] Filed: Dec. 23, 1986

[30] Foreign Application Priority Data

Dec. 27, 1985 [JP] Japan ................. 60-299363

[51] Int. Cl.$^5$ .............. C12N 15/79; C12N 15/81; C12N 15/09

[52] U.S. Cl. .................. 435/320.1; 435/69.1; 435/91; 435/171; 435/172.1; 435/172.3; 435/911; 435/940; 435/942; 536/27; 935/6; 935/8; 935/9; 935/22; 935/23; 935/24; 935/27; 935/28; 935/33; 935/36; 935/37; 935/59

[58] Field of Search ............ 435/69.1, 91, 171, 172.1, 435/172.3, 320, 911, 940, 942; 536/27; 935/6, 8, 9, 22, 23, 24, 27, 28, 33, 34, 36, 37, 59, 60, 66, 68, 69

[56] References Cited

PUBLICATIONS

Maniatis et al, 1982, Molecular Cloning:A Laboratory Manual, Cold Spring Harbor Laboratory.
Miyanohara et al, 1983, *PNAS* 80:1-5.
Kramer et al, 1984, *PNAS* 81:367.
Ronald A. Hitzeman et al., Expression of a Human Gene for Interferon in Yeast, *Nature,* vol. 293, pp. 717-722, (1981).
B. Meyhack et al., Two Yeast Acid Phosphatase Structural Genes are the Result of a Tandem Duplication and Show Different Degrees of Homology in their Promoter and Coding Sequences, *The Embo Journal,* vol. 1, No. 6, 675-680 (1982).
Jill Ferguson et al., *Gene,* vol. 16, pp. 191-197, (1981).
Hans Rudolph et al., *Proc. Natl. Acad. Sci. USA,* vol. 84, pp. 1340-1344 (1987).
Kenji Arima, et al., The Nucleotide Sequence of the Yeast PHO5 Gene: A Putative Precursor of Repressible Acid Phosphatase Contains a Signal Peptide, Nucleic Acids.
*Research,* vol. 11, No. 6, pp. 1657-1672, (1983).

*Primary Examiner*—Richard A. Schwartz
*Assistant Examiner*—Richard C. Peet
*Attorney, Agent, or Firm*—Wegner, Cantor, Mueller & Player

[57] ABSTRACT

Shuttle vectors including a DNA sequence of the yeast *Saccharomyces cerevisiae* including ars 1.2 micron ori and a marker gene for transformed yeast permitting synthesis of leucine by the transformant; adjacent to said ars 1 a DNA sequence of *Escherichia coli* which is either in EcoR1—PvuII or EcoR1—TthIII—I fragment of plasmid pBR322; and adjacent to the yeast marker gene the expression control region of the repressible acid phosphatase gene of yeast.

4 Claims, 2 Drawing Sheets

E: GENE ORIGINATED FROM ESCHERICHIA COLI

YEAST SHUTTLE VECTOR

The present invention relates to a novel shuttle vector, and more particularly, to a shuttle vector which contains a yeast gene and an Escherichia coli gene and carries the expression control region of the repressible acid phosphatase (said region being hereinafter referred to as "acid phosphatase promoter" or "acid phosphatase gene"), and can replicated in both *E. coli* and a yeast.

TECHNICAL BACKGROUND AND PRIOR ART

With recent active studies on genetic engineering technique, various recombinant DNAs and transformants therefrom have been developed. In the preparation of the recombinant DNAs, a vector for inserting a specific gene is used. Such a vector includes a vector which can replicate only in a certain microorganism, e.g. in *E. coli*, and a socalled shuttle vector which can replicate in two or more kinds of microorganism, e.g. in both *E. coli* and a yeast, or in both a certain microorganism (e.g. *E. coli*) and a certain animal cell. For instance, there has very recently been reported a shuttle vector which can replicate in both *E. coli* and a yeast: a vector utilizing a promoter of alcohol dehydrogenase (ADH1) which is usually used for the production of interferon with a yeast, to which promoter a gene encoding proteins of Hepatitits B virus surface antigen (hereinafter, referred to as "HBs antigen", or "HBsAg" or "s antigen") is inserted [cf. Nature, 298, 347–350 (22 Jul., 1982)]. However, the shuttle vector used in this method carries an ADH1 promoter and, when a recombinant DNA inserted with HBs gene is prepared by utilizing the vector and then a transformant is prepared from the recombinant DNA, the transformant can produce the desired HBs proteins only in a small amount.

The present inventors had extensively studied on an improved *E. coli*-yeast shuttle vector which can be recombined with various genes and can express them. As a result, it had been found that a specific shuttle vector having a yeast gene and an *E. coli* gene and carrying the repressible acid phosphatase promoter of the yeast has desired characteristics and is useful for recombining various genes under the control of the phosphatase promoter to prepare recombinant DNAs which can give various transformed yeasts [cf. Japanese Patent Application No. 145093/1982, U.S. Ser. No. 522,668, Canadian Patent Application No. 435007, European Patent publication No. 0103201, and Korean Patent Application No. 83-3854].

The above-mentioned shuttle vector includes shuttle vector pAT77 wherein a yeast DNA containing ars 1 (which is a DNA sequence necessary for the autonomous replication of the yeast), 2 μori (which is a DNA sequence necessary for the replication of 2 μm DNA, and Leu 2 (leucine-producing gene) as the yeast gene is combined with *E. coli* plasmid pBR322; and shuttle vectors derived from the shuttle vector pAT77 by treating it with an exonuclease BAL 31 to delete a part or whole of the structural gene of acid phosphatase and further optionally various regions upstream therefrom (usually from +1 to −100 bp), for example, shuttle vector pAM82 wherein upstream till −33 bp is deleted. The shuttle vector pAM82 has a structure as shown in the accompanying FIG. 1, wherein the thick line region is the gene originated from *E. coli* plasmid pBR322 and the remainder region is the gene of a yeast.

SUMMARY AND BRIEF DESCRIPTION OF THE INVENTION

In the shuttle vector pAM82 as mentioned above, the gene originated from *E. coli* is recombined in reverse direction downstream of the acid phosphatase promoter of yeast as shown in FIG. 1. As a result of the present inventors' further investigation on the shuttle vector pAM82, it has been found that a part of the gene originated from *E. coli* downstream of the acid phosphatase promoter exhibits a promoter activity in reverse direction to that of the acid phosphatase promoter within cells of yeast. That is, it has been found that when a gene to be expressed is inserted into said shuttle vector downstream of the acid phosphatase promoter, the desired gene is hardly expressed due to the said reverse promoter activity.

The present inventors have further studied as to the shuttle vector pAM82 and have found that the undesirable reverse promoter activity by the region of *E. coli* can be eliminated by treating the shuttle vector pAM82 with an appropriate restriction enzyme and thereby deleting a part of the gene originated from *E. coli* which is located downstream of the acid phosphatase promoter, and an improved shuttle vector having higher ability of expression of the desired gene can be obtained.

An object of the invention is to provide an improved shuttle vector having higher ability of expression of the desired gene which contains a yeast gene and an *E. coli* gene and carries the repressible acid phosphatase promoter of the yeast and loses a part of the region originated from *E. coli* downstream of the acid phosphatase promoter. Another object of the invention is to provide a shuttle vector which can be recombined with various genes under the control of the phosphatase promoter and can express the genes in higher efficiency. These and other objects and advantages of the invention will be apparent to those skilled in the art from the following description.

DETAILED DESCRIPTION OF THE INVENTION

The shuttle vector used in the present invention is a plasmid vector which contains both of a yeast gene and an *E. coli* gene and carries the repressible acid phosphatase gene of the yeast and further loses a part of the region downstream of the acid phosphatase promoter. This plasmid vector can replicate in both a yeast and *E. coli*, and can be used for the preparation of recombinant DNAs which are in turn used for the preparation of transformed yeasts, wherein the recombinant plasmids are prepared by using *E. coli* and then a yeast is transformed with the recombinant plasmid. The transformed yeasts thus prepared can produce the desired gene products on a large scale by propagation of the yeast. In the step of the transformation of a yeast, the vector may lose the *E. coli* gene.

The yeast gene used in this invention usually contains a DNA sequence which is necessary for replication of a plasmid in the yeast independently from chromosome, for instance, ars 1 and 2 μori, and contains optionally a gene useful as a selective marker of the transformed yeast. The selective marker includes, for example, a leucine-producing gene, a histidine-producing gene, a tryptophan-producing gene, a uracil-producing gene, an adenine-producing gene, or the like, which may be used alone or in combinations of two or more thereof.

The *E. coli* gene contains a DNA sequence necessary for the replication of the plasmid within cells of *E. coli*, for example, a DNA sequence of a replication initiating region of ColEI plasmid, and preferably contains a gene useful as a selective marker of the transformed *E. coli*. The selective marker includes, for example, an ampicillin-resistant gene, a kanamycin-resistant gene, a tetracycline-resistant gene, chloramphenicol-resistant gene, or the like, which may be used alone or in combinations of two or more thereof. Commonly used *E. coli* DNA is pBR322 which contains an ampicillin-resistant gene and a tetracycline-resistant gene.

The shuttle vector of the present invention is characteristic in that it carries the repressible acid phosphatase promoter of the yeast. This acid phosphatase promoter is usually a promoter of polypeptide of 60,000 dalton (P60) which constitutes the phosphatase.

Figure 3:
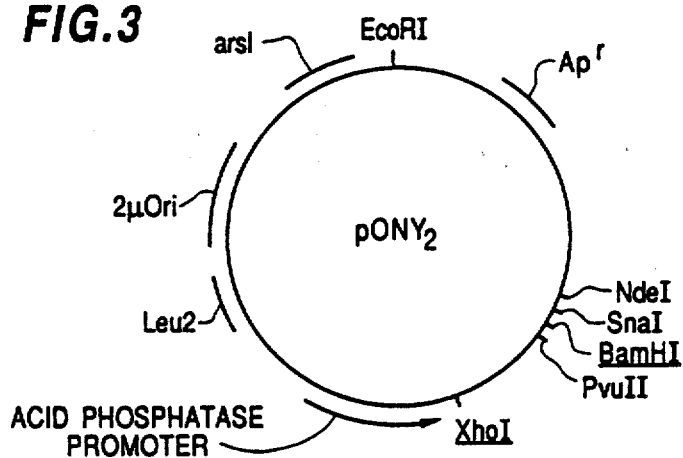
Figure 4:
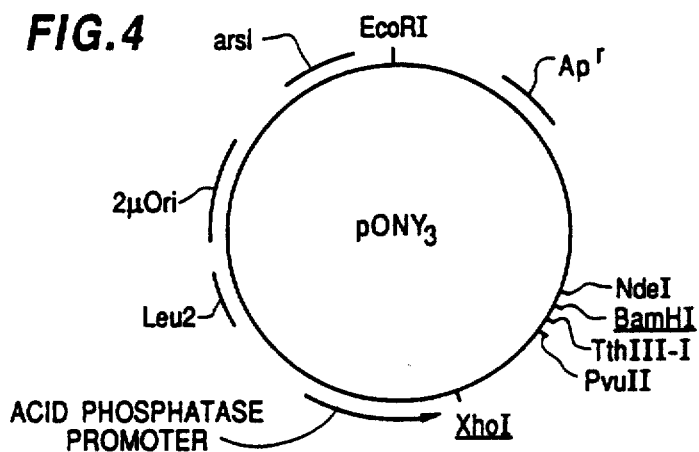
Figure 5:
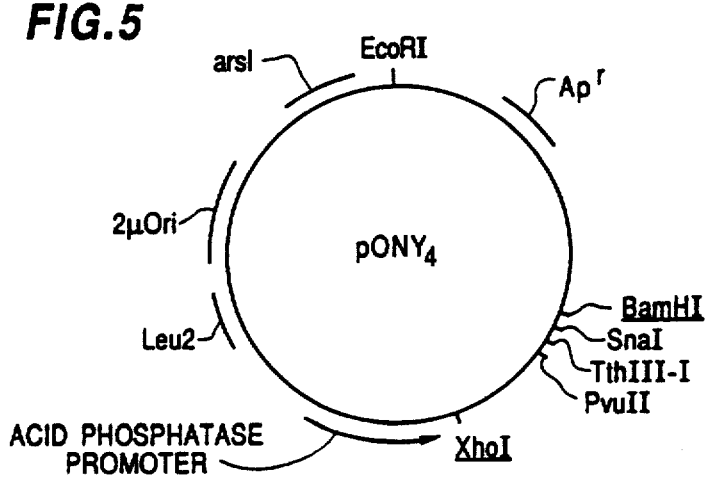

The shuttle vector of this invention can be prepared by treating the above-mentioned shuttle vector pAM82 with an appropriate restriction enzyme (e.g. PvuII), whereby a part of the gene originated from *E. coli* is deleted, adding BamHI linker at this enzyme site and then re-annealing. The resulting shuttle vector is designated as "pONY$_1$" (cf. FIG. 2). Likewise, the shuttle vector pAM82 is treated with other restriction enzymes, TthIII—I, SnaI, or NdeI, and each site thereof is converted into BamHI site to give the desired shuttle vector "pONY$_2$", "pONY$_3$" or "pONY$_4$", respectively (cf. FIG. 3 to 5).

In the shuttle vector pONY$_1$, the region (about 1.4 kb) originated from *E. coli* plasmid pBR322 of from SalI site (651) to PvuII site (2066) is deleted. Likewise, in pONY$_2$, pONY$_3$ and pONY$_4$, there are deleted the regions of from SalI site (651) to TthIII—I site (2219) (about 1.6 kb), of from SalI site (651) to SnaI site (2246) (about 1.6 kb), and of from SalI site (651) to NdeI site (2297) (about 1.6 kb), respectively.

The shuttle vectors pONY$_{1-4}$ of this invention can easily be cleaved by treatment with conventional enzymes such as XhoI and BamHI, and to the cleaved site is inserted various genes, by which various recombinant plasmids can be prepared. The recombinant plasmids can be used for transformation of yeasts by a conventional technique. Thus, the shuttle vector of this invention can widely be used in the genetic engineering field and hence is worthful for the industrial use. For instance, when the shuttle vector of this invention is inserted with an HBs gene to give a recombinant plasmid, and a yeast is transformed with the recombinant plasmid, the transformed yeast can produce HBs antigen in a large amount, said HBs antigen being immunologically idetical to natural HBs antigen obtained from human serum and hence being useful for preparing hepatitis B virus vaccine.

The present invention is illustrated by the following Example and Reference Example but should not be construed to be limited thereto.

EXAMPLE (1) Preparation of shuttle vector pAM82:

An EcoRI fragment of about 8,000 nucleotide pair (8 kb) containing a polypeptide (P60) gene of 60,000 dalton which constitutes the repressible acid phosphatase (available from Yeast S288C gene bank, Clarke, L. and Carbon, J., Cell, 9, 91–99, 1976) is inserted into the EcoRI site of known *E. coli* plasmid is digested with a restriction enzyme SalI and re-annealed with T$_4$ DNA ligase to give a plasmid pAT25 which is deficient from the SalI site to the acid phosphatase gene fragment 5.2 kb [said plasmid pAT25 being a plasmid consisting of a fragment (about 3.7 kb) of from EcoRI site to SalI site of pBR322 which contains the ampilicillin-resistant gene and a fragment (about 2.8 kb) of from EcoRI site to SalI site of the yeast acid phosphatase gene, wherein both fragments link at each corresponding terminal thereof].

Into the EcoRI site of the above pAT25 is inserted an EcoRI fragment (1.4 kb) containing ars 1 and Trp 1 gene which is prepared by treating a plasmid YRP7 (cf. Struhl, K., et al., Proc. Natl. Acad. Sci. U.S.A., 76, 1035–1039, 1979) with EcoRI to give a plasmid pAT26. Said ars 1-Trp 1 fragment has a single recognition site of a restriction enzyme HindIII within the Trp 1 gene.

Into the HindIII site of the above pAT26 is inserted a HindIII fragment containing a Leu 2 and 2 μori which is prepared by treating a plasmid pSLE 1 (cf. Tohe, A., et al., J. Bacteriol., 141, 413–416, 1980) with HindIII to give shuttle vector pAT77.

The pAT77 thus obtained (1 μg) is cleaved with SalI and then is treated with an exonuclease BAL31 (0.1 U) in a solution (50 μl) of 20 mM Tris-HCl (pH 8.2), 12 mM CaCl$_2$, 12 mM MgCl$_2$, 0.2M NaCl and 1 mM EDTA for 30 seconds to one minute. The reaction mixture is subjected to phenol extraction and ethanol precipitation in a usual manner, and the resulting precipitates are treated with XhoI linker (1 picomole) and T$_4$ DNA ligase in a usual manner for 12 hours.

*E. coli* $_x$1776 is treated with the above reaction mixture by the procedure as described in R. III. Curtiss et al., "Molecular Cloning of Recombinant DNA", eds. W. A. Scott and R. Werner, page 99, Academic Press (1977) so as to transform the *E. coli* $_x$1776 to give an ampicillin-resistant transformant. From the resulting transformant colonies, plasmid DNAs are prepared by the procedure as described by K. Matsubara (J. Virol., 16, 479, 1975). According to Maxam-Gilbert method (cf. Maxam, A. and Gilbert, W., Proc. Natl. Acad. Sci., 74, 560–564), the nucleotide sequence of the resulting DNAs is determined, and further, the region of the acid phosphatase gene deleted with BAL31 is determined. Among these DNAs, the desired plasmid pAM82 which is completely deficient in whole of the structural gene of the phosphatase is selected and isolated. The pAM82 carried on *Saccharomyces cerevisiae* AH 22 (i.e. *Saccharomyces cerevisiae* AH 22/pAM82) has been deposited at Fermentation Research Institute, Agency of Industrial Science and Technology, Japan under Budapest Treaty as "FERM BP-313".

Figure 1:
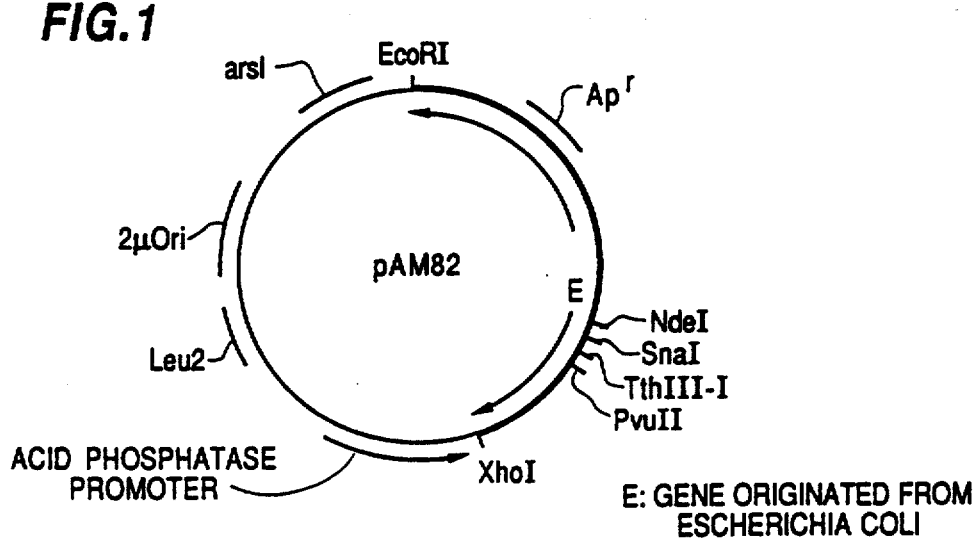
FIG. 1 shows the structure of shuttle vector pAM82.
Figure 2:
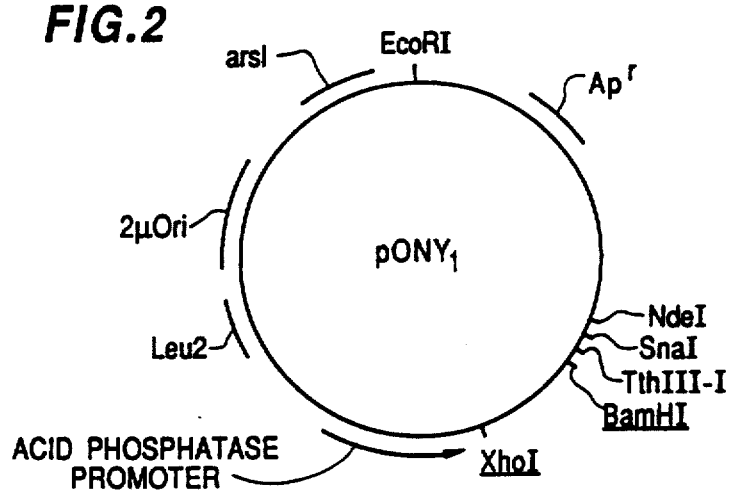
FIGS. 2 to 5 show each the structure of shuttle vector pONY$_1$ to pONY$_4$, respectively.

(2) Preparation of shuttle vector pONY$_1$:

The plasmid pAM82 as prepared above (1 μg) is cleaved by treating it with PvuII and the resulting fragment is reacted with T$_4$ DNA polymerase (1 U) in a mixture (50 μl) of 67 mM Tris-HCl (pH 8.8), 7.7 mM MgCl$_2$, 10 mM 2-mercaptoethanol, 6.7 μM EDTA, 16.6 mM (NH$_4$)$_2$SO$_4$, 330 μM dCTP, dATP, dGTP and dTTP at 37° C. for 30 minutes. The reaction mixture is subjected to phenol extraction and ethanol precipitation. The resulting DNA is reacted with BamHI linker (1 picomole) and T$_4$ DNA ligase for 12 hours. *E. coli* $_x$1776 is transformed with the reaction mixture. The ampicillin-resistant cells thus obtained are incubated, and there is isolated a plasmid (pONY$_1$) from the cells. The cleavage pattern of the plasmid with restriction enzymes XhoI and BamHI is determined, and the results are shown in FIG. 2.

In the same manner as described above except that other restriction enzymes TthIII—I, SalI and NdeI are used for the cleavage of pAM82 instead of PvuII, there are prepared other shuttle vectors pONY$_2$, pONY$_3$ and pONY$_4$, respectively.

By using the above shuttle vectors pONY$_1$ and pONY$_2$, the recombination of HBV DAN thereto is illustrated by the following Reference Example.

REFERENCE EXAMPLE (1) Preparation of HBV DNA:
(i) Preparation of virus DNA

A pooled blood plasma (700 ml) obtained from ten persons who are positive in HBsAg and HBeAg (subtype adr) is centrifuged at 5,000 r.p.m. for 20 minutes to remove undissolved materials. The resulting solution is centrifuged at 4° C., 18,000 r.p.m. for 8 hours, and the resultant precipitates are re-dissolved in 10 ml of a buffer (10 mM Tris-HCl, 0.1M NaCl, 1 mM EDTA, pH 7.5). The solution is added to the top of a centrifugal tube containing 30% sucrose, which is centrifuged at 4° C., 39,000 r.p.m. for 4 hours, and the resultant precipitates are re-dissolved in the same buffer as above.

In order to make easier the following operation, the above solution is subjected to the reaction with HBV DNA polymerase in a mixture (500 μl) of 67 mM Tris-HCl (pH 7.5), 80 mM NH$_4$Cl, 25 mM MgCl$_2$, 0.5% (w/v %, hereinafter the same) Tergitol NP-40 (manufactured by Sigma Co.), 0.1% 2-mercaptoethanol, 330 μM dCTP (deoxycytidine triphosphate), dGTP (deoxyguanosine triphosphate), dATP (deoxyadenosine triphosphate), and 0.5 μM α-[$^{32}$P] dTTP (deoxythiamine triphosphate) at 37° C. for 3 hours, and thereto is added the same volume of 100 mM EDTA solution. By the above DNA polymerase reaction, single-stranded region of the DNA is repaired to wholly double-strand to give a [$^{32}$P] labelled material. This material is added to the top of a centrifugal tube wherein 30%, 20% and 10% aqueous solutions of sucrose are packed in layers in this order, and it is centrifuged at 4° C., 39,000 r.p.m. for 4.5 hours.

In order to digest the proteins strongly bonded to the DNA, the precipitates obtained above are treated in a mixture (200 μl) of 1 mg/ml of pronase E (manufactured by Kaken Kagaku K.K.) and 0.2% aqueous sodium lauryl sulfate solution at 37° C. for 2 hours. The resulting DNA is extracted with phenol (200 μl) twice, and then washed with ether to remove phenol solvent to give a solution of HBV DNA. The DNA thus obtained has a specific radioactivity of 2.5×10$^6$ cpm/μg and can be used for digestion with restriction enzymes.

(ii) Cloning of HBV DNA:

The double-stranded circular HBV DNA obtained above is cloned by using λ-phage Charon 16A DNA as a vector and then is again cloned by using the known plasmid pACYC177 as a vector as follows.

HBV DNA (20 ng) is treated with endonuclease XhoI in a mixture (20 μl) of 10 mM Tris-HCl (pH 7.4), 7 mM MgCl$_2$, 100 mM NaCl and 7 mM 2-mercaptoethanol at 37° C. for 2 hours. The resulting mixture is extracted with phenol (200 μl) and washed with ether, and to the aqueous layer is added a double volume of cooled ethanol to precipitate DNA. The mixture is kept at −70° C. for one hour and then centrifuged at 10,000 r.p.m. for 5 minutes, and the precipitated DNA is isolated. The precipitate thus separated is dissolved in a mixture (5 μl) of 10 mM Tris-HCl (pH 7.4) and 1 mM EDTA. The HBV DNA and an equimolar amount of λ-phage Charon 16A DNA (having one recognition site of XhoI) obtained by cleavage with endonuclese XhoI in the same manner as described above are reacted with T$_4$ ligase [a mixture (10 μl) of 10 mM Tris-HCl (pH 7.4), 10 mM MgCl$_2$, 10 mM dithiothreitol, 100 μg/ml bovine serum albumin, 0.5 mM ATP and 0.5 μl enzyme preparation] at 4° C. for 18 hours. The reaction mixture is subjected to the extraction with phenol, treatment with ether and precipitation with ethanol in the same manner as described above, and the resulting precipitates are dissolved in a mixture (10 μl) of 10 mM Tris-HCl (pH 7.4) and 1 mM EDTA.

The thus annealed DNA is subjected to in vitro packaging operation to form λ-phage (cf. "Method in Enzymology", 68, 299–309), and further plaques (10$^4$) are formed therefrom on an L-agar plate (23 cm × 23 cm) by using E. coli DP50 supF (cf. Blattner, F.R. et al., Science, 196, 161, 1977) as an indicator. These plaques are subjected to plaque hybridization using $^{32}$P-labelled HBV DNA prepared above as a probe (cf. Science, 196, 180, 1977) in order to select the plaques formed from the phage having HBV DNA, by which a plural of the desired phages are separated.

(B) Re-cloning by using plasmid pACYC177 as a vector:

From the phage having HBV DNA obtained in the above (A), a phage DNA is prepared by using E. coli DP50 supF as a bacteria to be infected in the same manner as described in "Method in Enzymology", 68, 245–378, 1979. The DNA thus obtained is digested with XhoI under the same conditions as described above for 2 hours, and the resulting reaction mixture is subjected to an electrophoresis with 0.75% agarose gel to isolate HBV DNA (3.2 kb). The HBV DNA thus isolated is absorbed onto DEAE (diethylaminoethyl cellulose) paper (manufactured by Toyo Roshi, Japan) in order to separate from the vector DNA and then eluted with 1 M NaCl aqueous solution to give an HBV DNA having XhoI terminals at both ends.

Separately, plasmid pACYC177 (cf. Chang, A.C.Y., Cohen, S. N., J. Bacteriol., 134, 1141–1156, 1978) having a single XhoI cleavage site within kanamycin-resistant gene thereof is digested with XhoI likewise, and the product is purified by phenol extraction, ether treatment and ethanol precipitation in the same manner as described above.

The thus obtained pACYC177 cleaved with XhoI is mixed with XhoI-terminal HBV DNA obtained above in a molar ratio of 1:5, and the mixture is annealed with T$_4$ DNA ligase for 18 hours as descrived above.

The annealed DNA preparation (10 μl) obtained above is added to a liquid of E. coli (0.1 ml) which is prepared by treating a culture broth of E. coli X1776 [cf. R. III. Curtiss, et al., "Molecular Cloning of Recombinant DNA", eds. Scott, W. A. and Werner, R., page 99, Academic Press (1977)] by the procedure as described in M. V. Norgard, Gene, 3, 279 (1978), and the mixture is mixed well and allowed to stand at 0° C. for 25 minutes. The mixture is applied onto an L-agar plate containing ampicillin (20 μg/ml), α-biotine (1 μg/ml), diaminopimelic acid (100 μg/ml) and thymine (20 μg/ml)

and is incubated at 37° C. overnight. The resulting colonies are applied onto both an agar plate containing kanamycin (20 μg/ml) and an agar plate containing ampicillin (20 μg/ml), and the colonies which grow only on the agar plate containing ampicillin are selected. pA-CYC177 has an ampicillin-resistant gene and a kanamycin-resistant gene, but when it is inserted with HBV DNA at the XhoI site of the kanamycin-resistant gene, it loses the kanamycin-resistance. Accordingly, the selected colonies have a recombinant DNA of pA-CYC177-HBV DNA. From the colonies thus selected, a plasmid is prepared by the procedure as described in K. Matsubara (J. Virol., 16, 479, 1975). The plasmid thus obtained, i.e. the recombinant DNA of pA-CYC177-HBV DNA (which is designated "pHBV"), is treated with restriction enzyme XhoI to give total HBV DNA fragment (3.2 kb). Besides, when it is treated with XhoI and BamHI, there is obtained a fragment (about 1.3 kb) containing an HBsAg gene.

(2) Preparation of HBsAg gene-expression plasmids:

The plasmid pHBV is cleaved with BamHI, and the resulting HBsAg gene fragment (3 μg) is reacted with $T_4$ DNA polymerase (0.2 U) in a mixture (100 μl) of 67 mM Tris-HCl (pH 8.6), 6.7 mM $MgCl_2$, 10 mM 2-mercaptoethanol, 6.7 μM EDTA, and 16.7 mM $(NH_4)_2SO_4$ containing 200 μM dATP, dCTP, dTTP and dGTP for 30 minutes in order to fill-in the BamHI cleavage end. The reaction mixture is subjected to phenol extraction and ethanol precipitation and then subjected to linking raction with XhoI linker in a molar ratio of 1:10 with $T_4$ DNA ligase. After phenol extraction and ethanol precipitation, the resulting plasmid is treated with XhoI to give an HBsAg gene fragment (about 1.3 kb) having XhoI cleavage terminal at both ends. The fragment thus obtained is annealed with the shuttle vector $pONY_1$ cleaved with XhoI in a molar ratio of 5:1 by using $T_4$ DNA ligase, and *E. coli* X1776 is transformed with the reaction mixture obtained above to give a plasmid DNA.

The plasmid DNA is inserted with HBsAg gene in a correct direction downstream of the phosphatase promoter of the vector $pONY_1$, which plasmid is designted "$pONY-S_1$").

In the same manner as described above except that shuttle vector $pONY_2$ is used instead of $pONY_1$, there is prepared a recombinant plasmid "$pONY-S_2$".

(3) Preparation of transformed yeast:

The starting yeast is *Saccharomyces cerevisiae* AH22 [a leu 2 his4 can 1 (Cir+)], which has been deposited at Fermentation Research Institute, Agency of Industrial Science and Technology, Japan under Budapest Treaty as "FERM BP-312". The starting yeast is inoculated in YPD medium (100 ml) containing 2% polypeptone, 1% yeast extract and 2% glucose, and the mixture is incubated at 30° C. overnight, and thereafter, the cells are collected by centrifugation. The cells are washed with sterilized water (20 ml) and suspended in a solution (5 ml) of 1.2M sorbitol and 100 μg/ml zymolyase-60,000 (manufactured by Seikagaku Kogyo K. K., Japan), and the suspension is allowed to stand at 30° C. for about 30 minutes to give spheroplast. The spheroplast thus prepared is washed with 1.2M sorbitol solution three times, and then suspended in a solution (0.6 ml) of 2M sorbitol, 10 mM $CaCl_2$ and 10 mM Tris-HCl (pH 7.5). The suspension thus prepared is divided into a small test tube in a volume of 60 μl. To the suspension is added the recombinant plasmid $pONY-S_1$ (5 μg) as prepared in the above (3). After mixing well, 0.1M $CaCl_2$ (3 μl) is added thereto in a final concentration of 10 mM $CaCl_2$, and the mixture is allowed to stand at room temperature for 5 to 10 minutes. To the resulting mixture is added each 1 ml of 20% polyethylene glycol 4,000, 10 mM $CaCl_2$ and 10 mM Tris-HCl (pH 7.5), and the mixture is allowed to stand at room temperature for about 20 minutes. The resulting mixture (each 0.2 ml) is added to a medium (10 ml) [which consists of 22% sorbitol, 2% glucose, 0.7% yeast nitrogen base amino acid, 2% YPD, 20 μg/ml histidine, and 3% agar], which is kept at a constant temperature of 45° C. After gently mixing, the mixture is added in a layer onto a plate of minimal medium containing 1.2M sorbitol which is previously prepared and consists of 0.7% yeast nitrogen base amino acid, 2% glucose, 20 μg/ml histidine and 2% agar and is set thereon. The plate is incubated at 30° C. to give colony of a leucine-non-requiring yeast. The colony is incubated in a Burkholder minimal medium supplemented with histidine (20 μg/ml) [cf. Tohe, A. et al., J. Bacteriol., 113, 727–738 (1973)] to give the desired transformed yeast: *Saccharomyces cerevisiae* $YpONY-S_1$.

In the same manner as described above except that a recombinant plasmid $pONY-S_2$ is used instead of $pONY-S_1$, there is prepared a transformed yeast: *Saccharomyces cerevisiae* $YpONY-S_2$.

(4) Production of HBsAg with the transformed yeast:

Independent ten colonies of the transformed yeast obtained in the above (3) are inoculated into a Burkholder minimal medium supplemented with histidine (20 μg/ml) and incubated at 30° C. until logarithmic growth phase and then transferred to a semi-synthetic medium YASO [which consists of 0.05% magnesium sulfate, 0.5% ammonium sulfate, 4% fine granulated sugar, and 0.5% yeast extract] and further incubated at 26° C. The cells in logarithmic growth phase are collected by centrifugation, and thereto are added 50 mM phosphate buffer (sodium chloride added) (1 ml), 0.1% Tritone X-100, 1 mM PMSF (phenylmethylsulfonyl fluoride, $C_6H_5CH_2SO_2F$), and glass beads (diameter: 0.25-0.5 mm) (1 ml), and the mixture is vigorously shaked at 4° C. for 10 minutes, by which the cells are fractured, and HBsAg is extracted therefrom.

The extract thus obtained was tested with HBs antigen RIA kit (manufactured by Abbott, U.S.A.) in terms of the HBs antigen activity. The results are shown in Table 1.

As a control, the above procedure was repeated by using shuttle vector pAM82 instead of $pONY_1$, and the colonies (Nos. 14 and 15) were tested likewise. The results are also shown in Table 1.

TABLE 1

| Colony No. | Suttle vector | Recombinant plasmid | Amount of HBs antigen (μg/ml) |
|---|---|---|---|
| 1 | $pONY_1$ | $pONY-S_1$ | 3.30 |
| 2 | " | " | 3.03 |
| 3 | " | " | 2.79 |
| 4 | " | " | 2.45 |
| 5 | " | " | 2.61 |
| 6 | " | " | 2.01 |
| 7 | " | " | 3.77 |
| 8 | " | " | 3.53 |
| 9 | " | " | 3.02 |
| 10 | " | " | 2.99 |
| 11 | $pONY_2$ | $pONY-S_2$ | 3.90 |
| 12 | " | " | 4.15 |
| 13 | " | " | 4.27 |

TABLE 1-continued

| Colony No. | Suttle vector | Recombinant plasmid | Amount of HBs antigen (μg/ml) |
|---|---|---|---|
| 14 (Control) | pAM82 | pHS101A | 1.47. |
| 15 (Control) | " | " | 1.65 |

As is clear from the above results, in case of using the shuttle vector of this invention, there can be obtained HBs antigen in remarkedly higher yield in comparison with the case of using the known shuttle vector.

What is claimed is:

1. A shuttle vector comprising the following components:
   (a) a DNA sequence of the yeast *Saccharomyces cerevisiae* including ars 1, 2 μori and a marker gene for a transformed yeast permitting the synthesis of leucine by the transformant;
   (b) located adjacent to said ars 1, a DNA sequence of *Escherichia coli* which is an EcoRI—PvuII fragment of plasmid pBR322 having a size of about 2.3 kb and including a replication origin and a marker gene for transformed *E. coli* encoding resistance to ampicillin; and
   (c) located adjacent to the leucine gene, the expression control region of the repressible acid phosphatase gene of yeast containing, as its 3'end, up to the nucleotide which is −33 bp upstream from ATG (A:+1) of the acid phosphatase structural gene.

2. The shuttle vector of claim 1 that is pONY$_2$.

3. A shuttle vector comprising the following components:
   (a) a DNA sequence of the yeast *Saccharomyces cerevisiae* including ars 1, 2 μori and a marker gene for a transformed yeast permitting the synthesis of leucine by the transformant;
   (b) located adjacent to said ars 1 a DNA sequence of *Escherichia coli* which is an EcoRI—Tth III—I fragment of plasmid pBR322 having a size of about 2.1 kb and including a replication origin and a marker gene for a transformed *E. coli* encoding resistance to ampicillin; and
   (c) located adjacent to the leucine gene, the expression control region of the repressible acid phosphatase gene of yeast containing, as its 3'and, up to the nucleotide which is −33 bp upstream from ATG (A:+1) of the acid phosphatase structural gene.

4. The shuttle vector of claim 3 that is pONY$_1$.

* * * * *